US00PP18599P3

(12) United States Plant Patent
Tons

(10) Patent No.: US PP18,599 P3
(45) Date of Patent: Mar. 18, 2008

(54) OLIVE TREE 'KORONEIKI SELECTION OLINT'

(50) Latin Name: *Olea europaea*
Varietal Denomination: KORONEIKI OLINT

(76) Inventor: Joan Tons, 612 E. Gridley Road, Gridley, CA (US) 95948

( * ) Notice: Subject to any disclaimer, the term of this patent is extended or adjusted under 35 U.S.C. 154(b) by 0 days.

(21) Appl. No.: 11/093,775

(22) Filed: Mar. 29, 2005

(65) Prior Publication Data

US 2006/0225169 P1 Oct. 5, 2006

(51) Int. Cl.
*A01H 5/00* (2006.01)

(52) U.S. Cl. ..... Plt./158
(58) Field of Classification Search ..... Plt./158
See application file for complete search history.

(56) References Cited

U.S. PATENT DOCUMENTS

PP5,829 P 12/1986 Haas
PP7,750 P 12/1991 Zampini
PP10,641 P 10/1998 Sonnoli, Jr.
PP13,077 P2 10/2002 Fontanazza

OTHER PUBLICATIONS

Garden Web Glossary of Botanical Terms [online], retrieved on Jan. 8, 2007. Retrieved from the Internet <http://glossary.gardenweb.com/glossary/> 3 pages.*
California Olive Oil News, vol. 6, issue 12, Dec. 2003 [online], [retrieved on Apr. 18, 2006]. Retrieved from the Internet <http://www.oliveoilsource.com/newsletter/olivenews6–12.htm> 10 pages.*

* cited by examiner

*Primary Examiner*—Kent Bell
*Assistant Examiner*—June Hwu
(74) *Attorney, Agent, or Firm*—Mark D. Miller

(57) ABSTRACT

This new invention of an olive plant is characterized by its similarity to the 'Koroneiki Standard' (unpatented) from the island of Crete (Greece) from which it is a clonal selection, but is distinguished therefrom by producing a very small fruit early in the age of the tree (3rd leaf), better vigor, and higher productivity. The plants are ideally suited for olive oil production, mechanical harvesting and high density planting. The fruit matures in northern California during the third week of October.

4 Drawing Sheets

BACKGROUND OF THE NEW VARIETY

The present invention relates to a new and distinct variety of olive plant, *Olea europaea,* and will hereafter be denominated varietally as 'Koroneike Selection OLINT' and more particularly to an olive plant that produces fruit for harvest during the third week of October in the Gridley area of the northern Sacramento Valley in California and which is further distinguished as to novelty by having better vigor and fruit production than the parent 'Koroneiki Standard' (non-patented) variety. The variety 'Koroneiki Standard' has been used in Greece (Crete) for olive oil production over the past decade.

ORIGIN AND ASEXUAL REPRODUCTION OF THE NEW VARIETY

This new variety was vegetatively reproduced by cuttings after clonal selection (naturally occurring mutation) in Greece, and shipped and planted at two sites in Spain in 1995: Cataluna and Andelucia. After several years of evaluations, these clonal selections, chosen for the characteristics of medium vigor and very good production, were vegetatively propagated in 1997 and shipped in the United States. After completion of post-entry quarantine requirements in Oregon, in 2001 the vegetatively propagated material was shipped to Gridley, Calif. In 2004, 60,000 cuttings were asexually propagated.

SUMMARY OF THE NEW VARIETY

The new variety of olive tree is characterized by having the general characteristics of the 'Koroneiki Standard' variety but having the important distinction of having better vigor and very good production, maturing in northern California in the third week of October. Since this olive tree is smaller than the standard varieties (e.g. 'Manzanillo.'), the new variety is well suited for mechanical harvesting and high density planting (i.e. 670 plants/acre).

DETAILED DESCRIPTION

Figure 1:
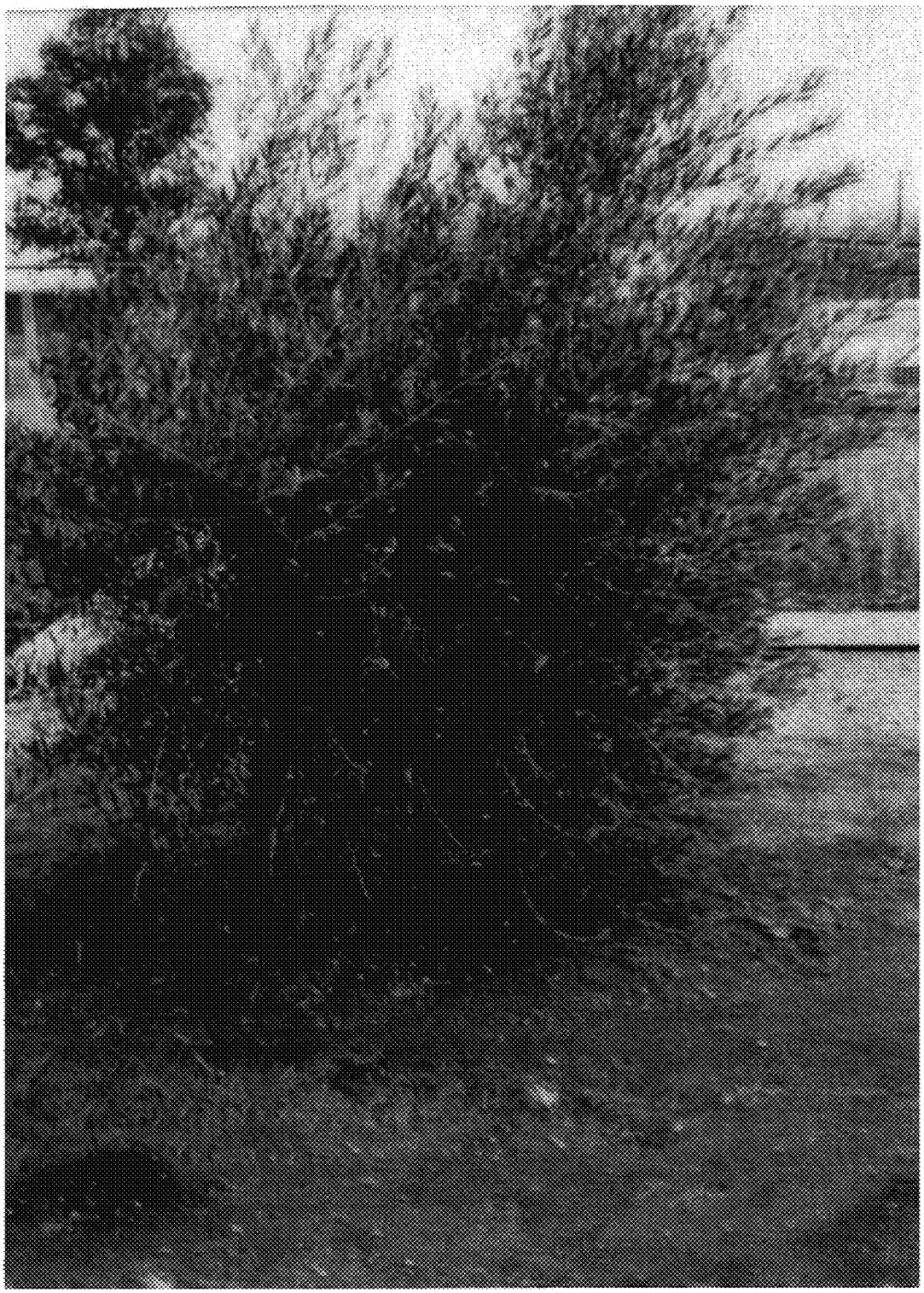
FIG. 1 is a color photograph exhibiting the overall shape of the tree and its appearance at third leaf (three year old tree).
Figure 2:
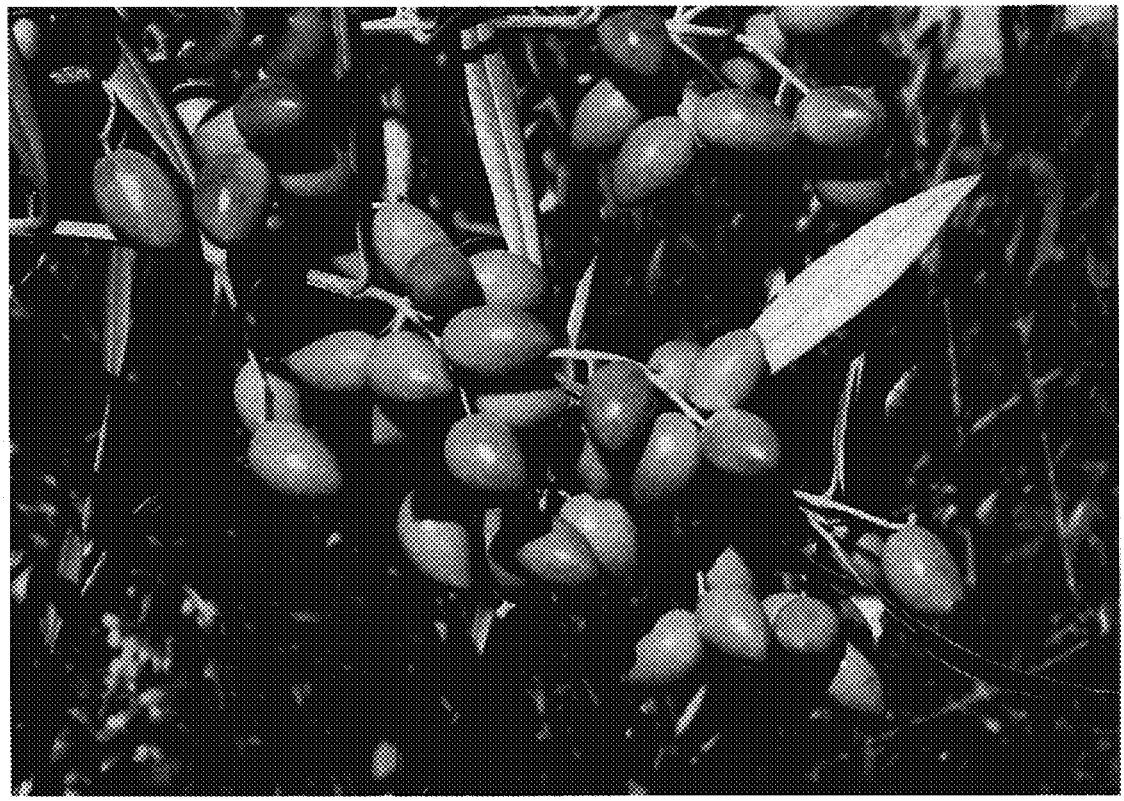
FIG. 2 is a color photograph of a typical branch of the new variety bearing fruit displaying clusters of olive fruit and their colors.
Figure 3:
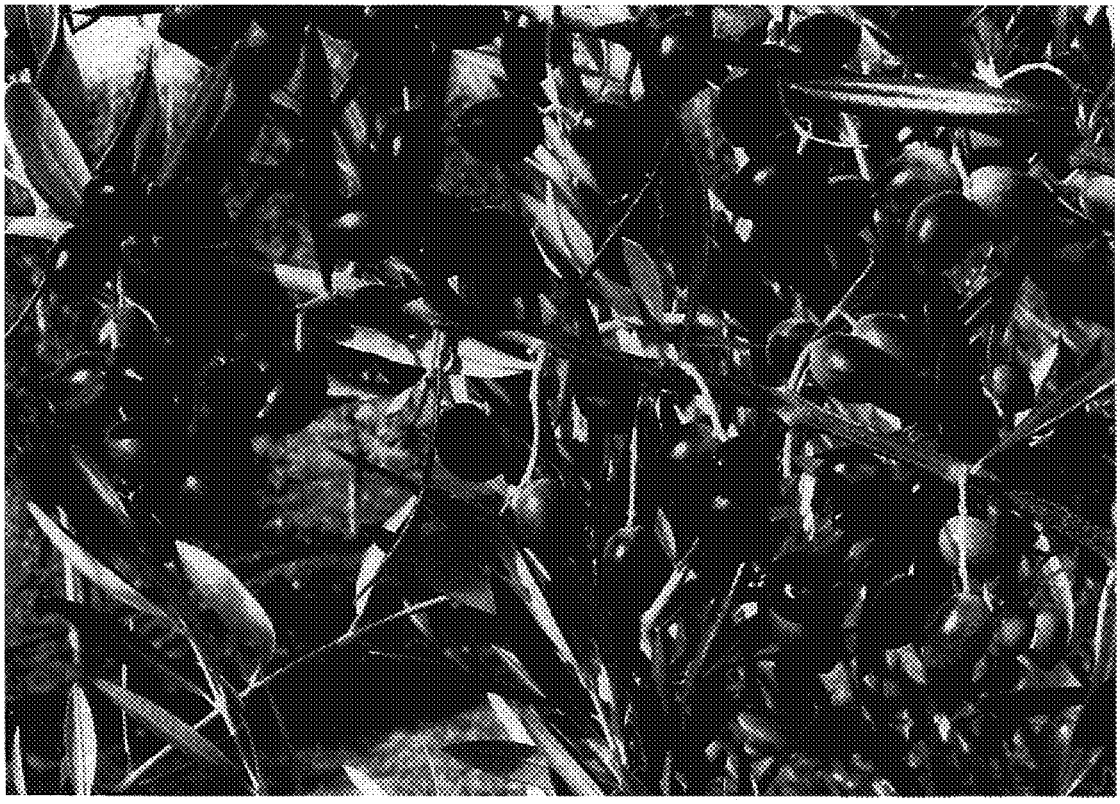
FIG. 3 is a color photograph of another typical branch of the new variety bearing fruit.
Figure 4:
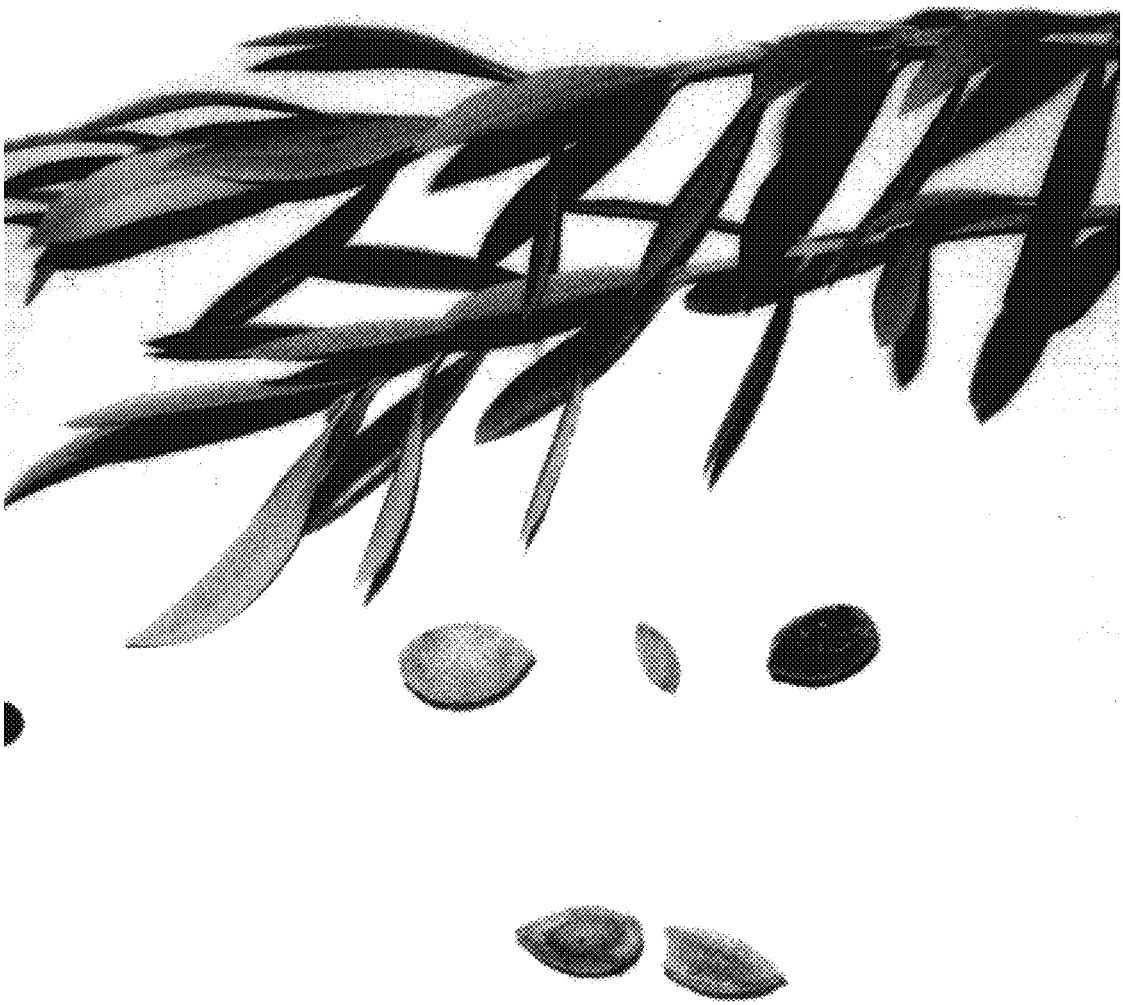
FIG. 4 is a color photograph showing the foliage in the upper portion, a green fruit on the left in the middle, a seed in the middle, and a ripe fruit on the right in the middle; at the bottom of the photograph is a fruit cut in half displaying the seed in one half on the left and the seed cavity and flesh at the seed cavity on the right.

Referring more specifically to the horticultural details of the new and distinct variety of olive trees, the following descriptions have been observed in a three year old tree under the ecological details prevailing at the site of origin which is located near Gridley, Calif. in the Sacramento Valley of northern California. All major color designations are by reference to the Dictionary of color by Maerz & Paul, First Edition, 1930. Common colors are also employed.

TREE

Height: small, 6–8 feet (183–244 cm).
Width: 2.5–3.5 feet (76–107 mm).
Trunk:
*Circumference.*—7.5 inches (19 cm), 12 inches (30 cm) above ground.
*Bark.*—Smooth.
*Color of bark.*—Dove grey (45-B-1). Vigor: medium good. Chilling: normal for olive trees in Northern California.
Figure: Open, scaffold branches significantly wide apart with no lateral branches
*Lenticels.*—Small.
Branches: 4.5 inches (11.43 cm) in circumference, 16 inches (41 cm) above crotch.
*Color.*—Mature: Rainette Green. (21-K-4). Immature: Certosa (20-L-3).
*Lenticels.*—Very small, moderate number.

LEAVES

Size: small.
Average Length: 45 mm (1.77 inch)
Average Width: 10 mm (0.39 inch)
Color:
*Upper surface.*—Mt. Vernon Green (23-J-8).
*Lower surface.*—Fern (21-I-7).
Shape: Elliptical.
Marginal From: Entire (smooth), without teeth or lobes.
Apex: Narrowly acute.
*Base: Cuneate.*
Surface texture:
*Upwardly disposed surface.*—Smooth.
*Downwardly disposed surface.*—Slightly pubescent.
Midvein:
*Color.*—Fern (21-I-7).
*Thickness.*—Less than 1 mm (0.04 inch).
Petiole:
*Size.*—Short, 4.3 mm (0.17 inch) in length.
*Color.*—Certosa (20-L-3).
Stipules:
*Size.*—Small, 1 mm (0.04 inch).
*Color.*—Certosa (20-L-3).

FLOWERS

Flower Buds: Small, slightly pubescent.
Average bud size: 1–2 mm (0.04–0.79 inch).
Date of First Bloom: Mid-May
*Size.*—Small, 2–4 mm (0.08–0.16 inch).
*Petal color.*—White (1-A-1).
Number of florets per inflorescence: 10–16.
Number of sepals: 4.
Number of petals: 4.
Fragrance: Mild.
Reproductive organs: 1 pistil; 18–22 stamens.
Pollen color: Yellow, Empire Y.(9-K-3).

FRUIT

Fruit: Borne in clusters of 2–3.
*Size.*—Small Length: 18–19 mm (0.70–0.74 inch). Width: 12–13 mm (0.47–0.51 inch).
Shape: Elliptical — oval.
Stem: Approx. 3 mm (0.12 in.).
Apex: Pointed.
Base: Truncate.
Background surface color: Grey Drab, Quaker Gray (21-B-1) ranging to Kara Dagh (56-A-2).
Skin:
*Thickness:*—1 mm (0.04 in.).
*Texture.*—Smooth.
*Color (immature).*—Chalcedony Y.(18-J-1).
*Color (mature).*—Royal Purple (43-K-11).
Flesh Color: Grey Drab (21-B-1).
*Cavity.*—Length: 10 mm (0.39 inch). Width: 4 mm (0.16 inch).
*Color of cavity.*—Olive Grey, Scotch Grey (21-A-2).
Seed:
*Small.*—Cling type.
*Length.*—13–14 mm (0.51–0.55 inch).
*Width.*—7 mm (0.27 inch).
*Shape.*—Elliptical and asymmetrical in shape.
*Surface texture.*—Slightly rough.
*Color of dried seed.*—Blue fox (47-E-1).
*Base.*—Truncate.
*Sides.*—Slightly asymmetrical unequal.
*Apex.*—Pointed.
*Ridges.*—Uneven.
*Suture.*—Marked.
*Tendency to split.*—None known.
Use: olive oil production.
*Keeping and shipping quality.*—Good.
*Resistance to disease.*—Verticilium and Peacock Spot.
*Harvesting maturity.*—Third week of October.

CHEMICAL ANALYSIS

TABLE 1

Olive Oil - 'Koroneiki selection OLINT'

| Type of Fatty Acid | Percentage of Total Oil Content |
|---|---|
| C16.0 Palmitic Acid | 11.4 ± .49 |
| C16.1 Palmitoleic Acid | 8.40 ± .18 |
| C18.0 Estaric Acid | 2.51 ± .29 |
| C18.1 Oleicv Acid | 76.6 ± .59 |
| C18.2 Linoleic Acid | 6.89 ± .74 |
| C18.3 Linolenic Acid | 0.93 ± .29 |

M/P ratio (Monosaturated Fat/Polysaturated Fat Ratio): 10.0 ± 1.02
Polyphenols (PPM Catecol): 600 ± 167
Bitterness 0.45 ± 09

What is claimed is:

1. A new distinct olive plant as described and illustrated that is characterized by having the general characteristics of the 'Koroneiki Standard' (unpatented) variety but is distinguished therefrom in that it has better vigor and higher productivity, the plants being ideally suited for olive oil production, mechanical harvesting and high density planting, with the fruit maturing in northern California in about the third week of October.

* * * * *